(12) United States Patent
Hong et al.

(10) Patent No.: US 11,173,116 B2
(45) Date of Patent: Nov. 16, 2021

(54) DRUG DELIVERY SYSTEM KIT COMPRISING AN ENZYME

(71) Applicant: INDUSTRY-ACADEMIC COOPERATION FOUNDATION, YONSEI UNIVERSITY, Seoul (KR)

(72) Inventors: Jin Kee Hong, Seoul (KR); Da Heui Choi, Seoul (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 0 days.

(21) Appl. No.: 16/508,543

(22) Filed: Jul. 11, 2019

(65) Prior Publication Data
US 2020/0016073 A1    Jan. 16, 2020

(30) Foreign Application Priority Data

Jul. 11, 2018  (KR) .......................... 10-2018-0080663
Jul. 11, 2019  (KR) .......................... 10-2019-0083761

(51) Int. Cl.
| | | |
|---|---|---|
| *A61K 9/00* | (2006.01) | |
| *D06M 16/00* | (2006.01) | |
| *A61L 15/44* | (2006.01) | |
| *A61K 9/70* | (2006.01) | |

(52) U.S. Cl.
CPC .......... *A61K 9/0092* (2013.01); *A61K 9/7007* (2013.01); *A61L 15/44* (2013.01); *D06M 16/003* (2013.01)

(58) Field of Classification Search
CPC .. A61K 9/0092; A61K 9/7007; D06M 16/003
See application file for complete search history.

(56) References Cited

FOREIGN PATENT DOCUMENTS

| | | | | |
|---|---|---|---|---|
| GB | 2367002 A | * | 3/2002 | .......... A61K 9/2866 |
| WO | 2017074262 A1 | | 5/2017 | |

OTHER PUBLICATIONS

Yiamsawas, D. et al. "Morphology-Controlled Synthesis of Lignin Nanocarriers for Drug Delivery and Carbon Materials" ACS Biomater. Sci. Eng. 2017, 3, 2375-2383 (Year: 2017).*
Ban, W. et al. "Influence of Natural Biomaterials on the Absorbency and Transparency of Starch-Derived Films: An Optimization Study" Ind. Eng. Chem. Res. 2007, 46, 6480-6485 (Year: 2007).*
Gessner, I. et al. "Hollow silica capsules for amphiphilic transport and sustained delivery of antibiotic and anticancer drugs" RSC Adv., 2018, 8, 24883-24892 (Year: 2018).*
Kim, T. et al. "Composite Porous Silicon-Silver Nanoparticles as Theranostic Antibacterial Agents" ACS Appl. Mater. Interfaces 2016, 8, 30449-30457 (Year: 2016).*
Park et al., Sohyeon, "Drug Loading and Release Behavior Depending on the Induced Porosity of Chitosan/Cellulose Multilayer Nanofilms," Molecular Pharmaceutics, DOI: 10.1021/acs.molpharmaceut.7b00371, Aug. 25, 2017, pp. 1-25.
Office Action dated Oct. 8, 2020 for corresponding case No. KR 10-2019-0083761. (pp. 1-6).

* cited by examiner

*Primary Examiner* — Andrew S Rosenthal
(74) *Attorney, Agent, or Firm* — Hauptman Ham, LLP

(57) ABSTRACT

The present invention relates to a drug delivery kit including an enzyme, and more particularly a drug delivery system using a drug delivery system kit, which includes a drug delivery system including a core and a coating layer; and an enzyme having a degradation activity against the coating layer.

5 Claims, 5 Drawing Sheets

Viability (%)

| Control (5.5) | TA film | Lignin film |
|---|---|---|
| 100 ± 2.24 | 93.53 ± 1.83 | 97.93 ± 5.31 |

| Control (7.4) | TA film | Lignin film |
|---|---|---|
| 100 ± 3.82 | 100.7 ± 1.16 | 93.37 ± 1.35 |

FIG. 9

Anticancer effect (%)

|  | pH 5.5 w/ enzyme | pH 5.5 | pH 7.4 w/ enzyme | pH 7.4 |
|---|---|---|---|---|
| TA film | 64.24 ± 0.46 | 85.02 ± 1.89 | 80.49 ± 3.50 | 76.63 ± 1.24 |
| Lignin film | 76.45 ± 4.52 | 72.38 ± 0.96 | 78.59 ± 3.50 | 64.22 ± 8.75 | ized into the body.
DRUG DELIVERY SYSTEM KIT COMPRISING AN ENZYME

CROSS-REFERENCE TO RELATED APPLICATIONS

This application claims priority under 35 U.S.C. § 119 to Korean Patent Application No. 10-2019-0083761, filed on Jul. 11, 2019, in the Korean Intellectual Property Office, the disclosure of which is incorporated herein by reference in its entirety.

TECHNICAL FIELD

The following disclosure relates to a drug delivery system kit including an enzyme, and more particularly, a drug delivery system kit including a drug delivery system including a core and a coating layer; and an enzyme having a degradation activity against the coating layer.

BACKGROUND

In the field of drug delivery systems, a lot of research has been intensively conducted to delay the burst release of a loaded drug and prevent side effects on tissues other than a certain target region using a drug delivery system exhibiting effective and selective drug release behaviors into the specific target region.

Recently, as this drug delivery system, there has been research that attempts to use plant-derived polymers such as cellulose, alginate, gum, pectin, and the like. Because the plant-derived polymers are present in abundant amounts in nature, they have price competitiveness, and have come into the spotlight as a next-generation drug delivery system due to their advantages such as non-cytotoxicity, natural degradation ability, and the like. In general, because plant cells have cell walls unlike animal cells, the plant cells may endure pressure such as turgor pressure, osmotic pressure, and the like. As a result, the plant-derived polymers extracted from these plant cells have very high stability. Therefore, the plant-derived polymers may be used as the drug delivery systems requiring physical stability to stably deliver various drugs, which is covered from low-molecular-weight compounds to high-molecular-weight protein drugs, to a target region.

Meanwhile, it is very important for an ideal drug delivery system to enhance the drug delivery efficiency and simultaneously reduce the side effects. Specifically, the drug delivery system should (1) control the release of a drug, (2) stably deliver the drug to a target region, (3) release the drug to have a medicinal effect when the drug reaches the target region, and (4) have no cytotoxicity.

In the previous research on drug delivery systems using a plant-derived polymer, the inside of a multilayer film was cross-linked using a method, which includes preparing a carboxymethylcellulose-derived multilayer film and chemically modifying the multilayer film, and a change in the drug release was checked due to structural and chemical changes caused accordingly (S. Park et al., Mol. Pharm. 2017, 14, 3322-3330). Also, a group of Deling Kong's researchers in China conducted research to prepare nanoparticles using alginate, load doxorubicin in the nanoparticles to check an anticancer effect of the particles, and release a drug loaded in the particles by means of light and an oxidation-reduction reaction (C. Zhang et al., Nanoscale 2017, 9, 3304-3314). In Sweden and Denmark, groups of researchers prepared a hollow shell using cell wall-derived substances, that is, cellulose nanofibers and pectin, and confirmed a possibility of controlling a degree of drug release, depending on a degree of penetration of the hollow shell according to the concentration of salts (T. Paulraj et al., Biomacromolecules 2017, 18, 1401-1410).

However, only cellulose and alginate-derived materials in the plant-derived polymers were applied in the conventional researches. These materials have limitations in endowing a drug delivery system with various characteristics, and have very few cases in which the drug delivery system was used to check a therapeutic effect of drugs.

In particular, the drug delivery system using the plant-derived polymer as described above has drawbacks in that a preparation method is complicated, and it is very difficult to control the stimuli which can control the drug release, such as light, oxidation-reduction reaction, or concentration of salts, in the body after the drug delivery system is administrated into the body.

Accordingly, there is a need for designing a drug delivery system that has high stability and no toxicity and may release a drug into a desired lesion site in the body so as to realize an ideal drug delivery system.

PRIOR-ART DOCUMENT

Non-Patent Document

Non-patent Document 1: S. Park et al., Drug loading and release behavior depending on the induced porosity of chitosan/cellulose multilayer Nanofilms. *Molecular Pharmaceutics* 2017, Vol. 14, No. 19, pp. 3322-3330

SUMMARY

An embodiment of the present invention is directed to providing a drug delivery system kit capable of overcoming the limitations of conventional drug delivery systems using a plant-derived polymer and realizing the smart drug release.

Another embodiment of the present invention is directed to providing a drug delivery system kit which has excellent price competitiveness and no toxicity and is capable of stably delivering a drug to a target location.

Still another embodiment of the present invention is directed to providing a drug delivery system kit which has a large amount of the loaded drug and is capable of controlling the release of the drug according to an enzyme into a target site.

Yet another embodiment of the present invention is directed to providing a method of preparing a hollow drug delivery system capable of controlling the release of a drug according to an enzyme.

Yet another embodiment of the present invention is directed to providing a method of treating a disease, which includes delivering a drug delivery system to a lesion site and releasing the drug.

To solve the above problems, in one general aspect, a drug delivery system kit according to the present invention is characterized in that the drug delivery system kit includes a core and a coating layer surrounding the core and composed of a multilayer thin film in which a first polymer electrolyte and a second polymer electrolyte are cross-laminated; and an enzyme, wherein the first polymer electrolyte and the second polymer electrolyte are complexed by any one or more attractions selected from the group consisting of electrostatic interaction and hydrophobic interaction.

According to one aspect of the present invention, the enzyme may have a degradation activity against the coating layer of the drug delivery system.

According to one aspect of the present invention, the core of the drug delivery system may include porous inorganic particles.

According to one aspect of the present invention, the core of the drug delivery system may include a hollow core having an empty inner space.

According to one aspect of the present invention, the first polymer electrolyte may include an ionic polypeptide, and the second polymer electrolyte may include an enzymatically degradable phenolic polymer.

According to one aspect of the present invention, the second polymer electrolyte may include lignin.

According to one aspect of the present invention, when the drug delivery system comes into contact with the enzyme, the release of a drug may be suppressed in a range of pH 6.5 to 9, and the drug may be rapidly released in a range of pH 4 to 6.

In another general aspect, a method of preparing a hollow drug delivery system according to the present invention includes (a) cross-laminated a first polymer electrolyte and a second polymer electrolyte on surfaces of porous inorganic particles to prepare composite particles having a multilayer thin film coating layer formed thereon; and (b) dissolving the porous inorganic particles from the composite particles to form a hollow core.

According to one aspect of the present invention, the porous inorganic particles may include a metalloid carbonate.

According to one aspect of the present invention, the method of preparing a hollow drug delivery system may further include containing a drug in pores of the porous inorganic particles.

According to one aspect of the present invention, the step (b) may be carried out by treating the composite particles with a chelating agent.

In still another general aspect, a method of treating a disease according to the present invention includes administering a drug delivery system to deliver the drug delivery system to a lesion site, wherein the drug delivery system includes a core and a coating layer surrounding the core and composed of a multilayer thin film in which a first polymer electrolyte and a second polymer electrolyte are cross-laminated, wherein the first polymer electrolyte and the second polymer electrolyte are complexed by any one or more attractions selected from the group consisting of electrostatic interaction and hydrophobic interaction; and treating the drug delivery system with an enzyme.

According to one aspect of the present invention, the enzyme may have a degradation activity against the coating layer of the drug delivery system.

According to one aspect of the present invention, the disease may include any one selected from a cancer, an inflammatory disease, a skin disease, and a metabolic disease.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which:

FIG. 9 shows the test results of anticancer effects of the drug delivery system kit according to one embodiment of the present invention.

DETAILED DESCRIPTION OF EMBODIMENTS

Figure 1:
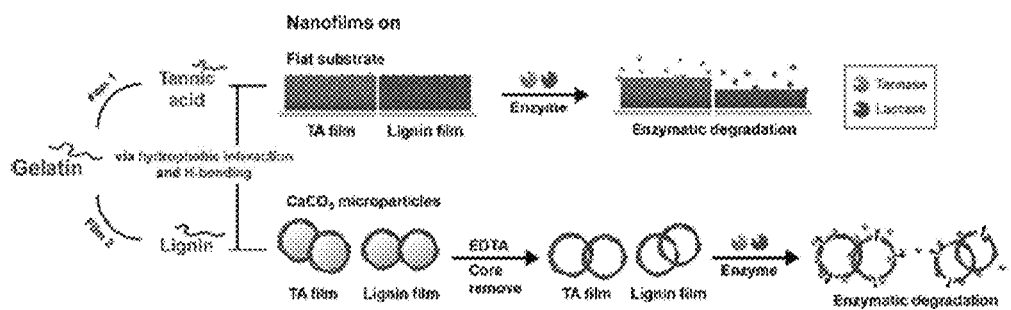
FIG. 1 is a schematic diagram showing a method of preparing a drug delivery system according to one embodiment of the present invention and a process of treating the prepared drug delivery system with an enzyme.

Hereinafter, the present invention will be described in detail with reference to the accompanying drawings. The drawings presented hereinbelow are shown as one example to sufficiently provide the scope of the present invention to those skilled in the art. Therefore, it should be understood that the present invention may be embodied in various forms, but is not intended to be limiting in the drawings presented hereinbelow. In this case, the drawings presented hereinbelow may be shown in an exaggerated manner to make the scope of the present invention more clearly apparent.

Unless otherwise defined, the technical and scientific terms used in the specification of the present invention have the same meaning as commonly understood by one of ordinary skill in the art to which the present invention pertains. In the following description and the accompanying drawings, a description of known functions and configurations, which may unnecessarily obscure the subject matter of the present invention, will be omitted.

Also, the singular forms "a," "an," and "the" used in the specification of the present invention refer to those encompassing plural referents unless the context clearly dictates otherwise.

In addition, the units used without any particular comments in the specification of the present invention are based on weight. For example, the units of % or percentage refer to a percent (%) by weight ratio or weight percentage.

Also, unless otherwise defined in this specification of the present invention, an average particle diameter of particles refers to a $D_{50}$ value obtained using a particle size analyzer.

Additionally, a numerical range used in this specification of the present invention is meant to include its upper and lower limits and all possible combinations of all values falling within these limits, increments logically derived from the shapes and widths of defined ranges, all values defined therefrom, and upper and lower limits of the numerical ranges defined in different types. As one example, it should be understood that, when the molecular weight is defined in a range of 100 to 10,000, particularly in a range of 500 to 5,000, a numerical range of 500 to 10,000 or 100 to 5,000 is also described in this specification of the present invention. Unless otherwise particularly defined in this specification of the present invention, all values falling out of this numerical range that may occur due to the rounding off of the experimental errors or values also fall within the defined numerical ranges.

Also, in the specification of the present invention, the expression "comprise(s)" is intended to be open-ended transitional phrases having an equivalent meaning with "include(s)," "have," "has," "contain(s)," and "is(are) characterized by," and does not exclude elements, materials, or steps, all of which are not further recited herein. Also, the expression "consist(s) essentially of" means that one element, material or step, which is not recited in combination with the other elements, materials or steps, may be present at an amount having no unacceptably significant influence on at least one basic and novel technical idea of the invention. Also, the expression "consist(s) of" means the presence of only the elements, materials or steps defined herein.

In addition, in the specification of the present invention, the hydrophilicity and hydrophobicity mean a water-loving character and a water-hating character, respectively, but refer to a relative concept when the hydrophilicity and hydrophobicity are used at the same time. As one specific example, in the case of a hydroxyl group (—OH) and an alkyl group, the hydroxyl group refers to a hydrophilic group, and the alkyl group refers to a hydrophobic group.

The present invention relates to a drug delivery system kit which has no toxicity and high stability in the body, and is capable of controlling the release of a drug using an enzyme having a degradation activity against a drug delivery system.

The drug delivery system kit according to the present invention is characterized in that the drug delivery system kit includes a core and a coating layer surrounding the core and composed of a multilayer thin film in which a first polymer electrolyte and a second polymer electrolyte are cross-laminated; and an enzyme, wherein the first polymer electrolyte and the second polymer electrolyte are complexed by any one or more attractions selected from the group consisting of electrostatic interaction and hydrophobic interaction.

According to one aspect of the present invention the present invention, the core of the drug delivery system is used to form a coating layer composed of a multilayer thin film in which a first polymer electrolyte and a second polymer electrolyte are cross-laminated on a surface thereof. Preferably, the core of the drug delivery system may include porous inorganic particles. The porous inorganic particles may be secondary inorganic particles formed by aggregation of a plurality of primary inorganic particles. In this case, as the primary inorganic particles are aggregated, a number of pores may be formed between the inorganic particles to exhibit porosity.

Also, the porous inorganic particles may be metal and metalloid oxides or carbonates, for example, be one or two or more mixed porous inorganic particles selected from $CaCO_3$, $SiO_2$, $Al_2O_3$, $TiO_2$, MgO, $Fe_2O_3$, $ZrO_2$, $SnO_2$, $CeO_2$, $BaTiO_3$, $HfO_2$, and $SrTiO_3$. Preferably, the porous inorganic particles may include a metalloid carbonate, and may have an average particle diameter of 0.1 to 100 μm, particularly 1 to 50 μm, and more particularly 2 to 10 μm, but the present invention is not limited thereto.

Preferably, the porous inorganic particles of the present invention may include porous calcium carbonate ($CaCO_3$) having an average particle diameter within this diameter range. Preferably, the porous calcium carbonate may be secondary calcium carbonate particles formed by aggregation of primary calcium carbonate particles having a diameter of 10 nm to 500 nm. The porous calcium carbonate ($CaCO_3$) may be prepared using a known co-precipitation method, but the present invention is not limited thereto. Also, a method of preparing the porous calcium carbonate ($CaCO_3$) is not limited, but, as one specific example, porous $CaCO_3$ particles may be obtained by stirring calcium chloride ($CaCl_2$)) and sodium carbonate ($Na_2CO_3$) solutions to form secondary particles in which primary $CaCO_3$ particles are aggregated, and centrifuging, washing and drying the secondary particles. In this case, the particle sizes and shapes of the porous $CaCO_3$ particle may be adjusted according to the concentration and stirring speed of the calcium chloride ($CaCl_2$)) and sodium carbonate ($Na_2CO_3$) solutions. In this case, a lyophilization process may be included after the washing so as to prevent recrystallization.

The core including the porous inorganic particles includes a number of pores, and thus may contain a large amount of a drug in the pores, and simultaneously provide a high specific surface area to a surface of the core, thereby inducing the cross-laminating of the first polymer electrolyte and the second polymer electrolyte on a surface of a core layer more effectively. As a result, because it is possible to form a coating layer having a sufficient thickness, the drug may be loaded in the inside of the core of the drug delivery system as well as the coating layer, thereby further increasing an amount of the loaded drug.

According to one aspect of the present invention, the thickness of the coating layer may be in a range of 1 to 1,000 nm, particularly 10 to 500 nm, and more particularly 20 to 100 nm, but the present invention is not limited thereto. When the coating layer has a thickness within this thickness range, the drug delivery system can reach a target region with a stable structure in the body, and may have a large amount of the loaded drug.

According to one aspect of the present invention, the core of the drug delivery system may include a hollow core having an empty inner space, which is formed by dissolving the porous inorganic particles. The hollow core having an empty inner space may be prepared by forming a coating layer on a surface of the core, followed by treatment of the coating layer with a known chelating agent to remove the core. A method of preparing the hollow core having an empty inner space may not limited, but, as a specific example, the hollow core may be prepared by cross-laminating a first polymer electrolyte and a second polymer electrolyte on a surface of the core including the porous $CaCO_3$ particles to prepare composite particles in which a multilayer thin film coating layer is formed, followed by treatment of the composite particles with an aqueous solution including a chelating agent to chelate calcium ($Ca^{2+}$) ions in the core so as to dissolve the porous $CaCO_3$ particles.

Also, the chelating agent may, for example, include any one or chelating agent or a combination of two or more selected from ethylenediaminetetraacetic acid (EDTA) and diethylenetriamine pentaacetic acid (DTPA), but the present invention is not limited thereto.

The drug delivery system according to one aspect of the present invention includes the hollow core having an empty inner space, thereby remarkably increasing an amount of the loaded drug in the core. In this case, the loaded drug may be allowed to stably deliver in the body due to the coating layer so that a sufficient amount of the drug can reach a target region.

The coating layer of the drug delivery system according to one aspect of the present invention is composed of the multilayer thin film in which the first polymer electrolyte and the second polymer electrolyte are cross-laminated, and thus may be degraded by the enzyme to release the drug loaded in the core and the coating layer from the drug delivery system.

In particular, the first polymer electrolyte and the second polymer electrolyte may be ionic polymers having different charges, and may optionally include a hydrophobic residue in the molecule. As the aforementioned first polymer electrolyte and second polymer electrolyte are cross-laminated on a surface of the core, the two electrolytes may be complexed by any one or more attractions selected from the group consisting of electrostatic interaction and hydrophobic interaction so as to form a coating layer. Preferably, the first polymer electrolyte and the second polymer electrolyte may have different charges, and simultaneously include a hydrophobic residue in the molecule. In this case, the coating layer may be more compactly formed due to the attraction caused by electrostatic and hydrophobic interactions between the two electrolytes. Therefore, the drug delivery system may maintain a stable structure in the body, and remarkably suppress early release of the drug before the coating layer is degraded by the enzyme. Also, because the hydrophobic drug may be effectively loaded in a plurality of hydrophobic domains in the coating layer formed by the hydrophobic residue, the drug delivery system may have an effect of further increasing an amount of the loaded drug.

In one preferred aspect of the present invention, the first polymer electrolyte may include an ionic polypeptide, and the second polymer electrolyte may include an enzymatically degradable phenolic polymer.

The ionic polypeptide is a material in which amino acids are linked via a peptide bond, and specific examples of the ionic polypeptide may be one or a mixture of two or more selected from gelatin, collagen, fibrinogen, silk fibroin, casein, elastin, laminin, fibronectin, and poly-L-lysine. Preferably, gelatin may be used, but the present invention is not limited thereto. The ionic polypeptide is dissociated in water to exhibit an ionic character. For example, when the gelatin is used as the first polymer, the gelatin may exhibit a cationic character in an aqueous solution of less than pH 7, particularly pH 5 to 7, and may form a coating layer through electrostatic interaction with an enzymatically degradable phenolic polymer in the second polymer electrolyte exhibiting an anionic character. On the other hand, the gelatin may exhibit a weak cationic character in an aqueous solution of pH 7 or more, particularly pH 7 to 9. In this case, the gelatin may form a coating layer by means of hydrophobic interaction between a proline amino acid structure in the gelatin molecule and the enzymatically degradable phenolic polymer.

The second polymer electrolyte includes an enzymatically degradable phenolic polymer which is degraded by the enzyme, and thus may rapidly release the drug loaded in the core and the coating layer of the drug delivery system as the enzymatically degradable phenolic polymer in the coating layer is degraded when the drug delivery system comes into contact with the enzyme.

In one preferred aspect of the present invention, the second polymer electrolyte may include lignin or tannic acid, and may preferably include alkali-treated water-soluble lignin. The lignin and tannic acid are plant-derived polymers which are present in abundant amounts in nature and are inexpensive, and also are environmentally friendly, and have excellent safety in the human body. Therefore, the drug delivery system having superior safety without any cytotoxicity may be provided.

Also, the lignin and tannic acid include a large amount of hydroxyl groups in the molecule, and thus may effectively perform the cross-laminating by means of electrostatic interaction with the cationic polypeptide, which makes it possible to form a coating layer more stably.

In particular, when the second polymer electrolyte includes the lignin, the coating layer of the drug delivery system prepared with respect to the tannic acid may be relatively thinly and uniformly formed, and a structure of the coating layer is more stable and has a large amount of the loaded drug when the drug delivery system having a hollow core having an empty inner space is prepared by treating the coating layer with a chelating agent after formation of the coating layer.

As one specific example of a method of forming a coating layer using the first polymer electrolyte and the second polymer electrolyte, the drug delivery system in which the first polymer electrolyte and the second polymer electrolyte are cross-laminated and complexed by means of electrostatic interaction may be prepared by adding a core to an aqueous ionic polypeptide solution serving as the first polymer electrolyte to attach a first polymer to a surface of the core, and adding the first polymer to an aqueous second polymer electrolyte solution to attach a second polymer. In this case, when the first polymer and second polymer include a hydrophobic residue, the coating layer may be more compactly formed by means of hydrophobic interaction, thereby further improving structural stability of the drug delivery system, but the present invention is not limited thereto.

Also, the cross-laminating using the first polymer electrolyte and the second polymer electrolyte may be repeatedly performed once or more, particularly 2 to 10 times, but the present invention is not limited thereto. The drug delivery system including a core and a coating layer surrounding the core and composed of a multilayer thin film may be prepared through the cross-laminating.

In addition, the second polymer may have a weight average molecular weight of 1,000 g/mol or more, particularly 5,000 to 1,000,000 g/mol, and more particularly 10,000 to 500,000 g/mol, but the present invention is not limited thereto. When the second polymer is used at an amount within this range, the coating layer may be more compactly formed due to the excellent interaction with the first polymer. Therefore, the drug may be delivered while maintaining high stability without any early leakage of the drug until the drug delivery system reaches a target region in the body.

In one aspect of the present invention, the enzyme has a degradation activity against the coating layer of the drug delivery system. As the drug delivery system is treated with the enzyme as soon as the drug delivery system reaches the target region, degradation of the coating layer may be induced to allow the release of the drugs. Specific examples of the enzyme may include laccase and tannase, which have a degradation activity against lignin and tannic acid, respectively. The enzyme has no cytotoxicity and is harmless to the human body. In particular, the laccase rapidly oxidizes a hydroxyl group of lignin, and the tannase hydrolyzes an ester bond of tannic acid to degrade the tannic acid into gallic acid and glucose. Therefore, when the coating layer including the lignin or tannic acid is rapidly degraded by the enzyme, it is possible to rapidly release the drug in the target region.

As the compact coating layer surrounding the core is formed using the plant-derived polymer, that is, lignin or tannic acid, the drug delivery system kit including the drug delivery system and the enzyme according to the present invention has an excellent effect of preventing leakage of the drug until the drug delivery system reaches a target region without naturally degrading the drug delivery system in the body. Besides, the enzyme having a degradation activity against the coating layer may be used to control a drug behavior of the drug delivery system.

In the case of conventional drug delivery system including a low-molecular-weight phenolic material such as epigallocatechin gallate (EGCG) as the coating layer is easily degraded in the body, all of the drug may be released before the drug delivery system reaches the target region, or it is difficult to apply stimuli to the drug delivery system even when the drug delivery system reaches the target region. However, in the drug delivery system kit according to the present invention, the drug delivery system capable of realizing the smart drug release is provided, which may suppress the rapid burst effect of the drug, solve a problem such as difficulty in controlling the release of the drug in a lesion site, and control the release of the drug by administration of the enzyme.

Also, because the drug delivery system according to the present invention does not use a low-molecular-weight phenolic material but a relatively high-molecular-weight, enzymatically degradable phenolic material having a weight average molecular weight within this molecular weight range, the enzymatically degradable phenolic material may enhance electrostatic and hydrophobic interactions with ionic peptides, and may be cross-laminated on a surface of the core to form a multilayer thin film, which makes it possible to form a very compact coating layer. Therefore, an effect of suppressing the drug release may be further improved until the drug delivery system reaches the target region.

In addition, when the plant-derived enzymatically degradable phenolic polymer is used as described above, the drug delivery system is not spontaneously degraded in the body but degraded only by treatment with the enzyme. Therefore, the drug release does not happen until the drug delivery system reaches the target region, and the enzymatically degradable phenolic polymer may be degraded by treatment with the enzyme so that the loaded drug can be released at the same time, thereby maximizing a therapeutic effect.

Depending on the types of the enzymatically degradable phenolic polymer in the second polymer electrolyte, the drug delivery system according to one preferred aspect of the present invention may be a first aspect in which a coating layer, which is composed of a multilayer thin film in which a first polymer electrolyte including gelatin and a second polymer electrolyte including lignin are cross-laminated, surrounds a core; or a second aspect in which a coating layer, which is composed of a multilayer thin film in which a first polymer electrolyte including gelatin and a second polymer electrolyte including tannic acid are cross-laminated, surrounds a core.

The drug delivery system kit according to one aspect of the present invention includes the drug delivery system of the first aspect and a laccase enzyme. When the drug delivery system comes into contact with the enzyme, it is characterized that the drug release may be suppressed in a range of pH 6.5 to 9, and the drug may be rapidly released in a range of pH 4 to 6.

The laccase enzyme has an excellent degradation activity against lignin under a relatively acidic condition, and thus may degrade the coating layer including lignin and rapidly release the loaded drug in a range of pH 4 to 6, particularly pH 4.5 to 5.5. On the other hand, the drug delivery system may maintain a stable structure without any degradation of the coating layer due to the low degradation activity of the enzyme against lignin at a relatively basic condition, that is, in a range of pH 6.5 to 9, particularly pH 7 to 8. Therefore, the release of the drug may be suppressed, and a sufficient amount of the drug may be effectively delivered to a target region.

Also, the drug delivery system kit including the drug delivery system of the second aspect and the tannase enzyme is characterized in that, when the drug delivery system comes into the tannase enzyme, like the drug delivery system of the first aspect, the drug release is suppressed in a range of pH 6.5 to 9, and the drug is rapidly released in a range of pH 4 to 6. In addition, because the tannic acid in the drug delivery system of the second aspect has a characteristic of being self-oxidized at pH 7 or more, the coating layer may be self-degraded in this pH range and release the drug.

As one non-limiting example, the enzyme may be included in the drug delivery system. When the enzyme is included in the drug delivery system so that the drug delivery system is exposed to an acidic environment, the enzyme may have a degradation activity, and induce the degradation of the coating layer of the drug delivery system to allow the release of the loaded drug. As another non-limiting example, the enzyme may be administered through various routes of oral and parenteral administration, and may, for example, be administered by oral, percutaneous, intrarectal, intravenous, intramuscular, subcutaneous, intrauterine dural, or intracerebroventricular injection, but the present invention is not limited thereto. As one specific example, when the drug delivery system kit consisting of the drug delivery system and the enzyme is orally administrated, the drug delivery system of the first aspect may maintain a stable structure in the mouth having a neutral condition, and may reach the stomach through the esophagus. The drug delivery system kit which has reached the stomach may release the drug because the coating layer of the drug delivery system is degraded as the enzyme exhibits a degradation activity in the stomach having an acidic condition. When the drug delivery system kit may be applied to drugs for oral administration for treating stomach-related diseases such as gastritis, and the like, the drug delivery system kit may exhibit an excellent therapeutic effect.

Also, as one example of a method of parenterally administrating the drug delivery system kit, when the drug delivery system kit is introduced into the body by intravenous injection, the drug delivery system may maintain a stable structure without any early release of the drug due to degradation of the coating layer in normal tissue cells of pH 6.5 to 7 while moving through blood vessels. On the other hand, when the drug delivery system reaches cancer tissue cells having a relatively acidic condition of pH 5 to 6, the degradation activity of the enzyme may be expressed, and the coating layer may be degraded at the same time to rapidly release the drug. In this way, the drug delivery system may be used for the drug delivery system kit having an ability to target cancer so as to induce selective death of cancer cells, minimize side effects of anticancer drugs, and maximize a therapeutic effect on cancer as well.

In this case, the enzyme may be administrated together with the drug delivery system, or may be sealed in the drug delivery system, or may be administrated after administration of the drug delivery system. To improve bioavailability of the enzyme, polyethylene glycol may be covalently bonded, that is, PEGylated to the enzyme, but the present invention is not limited thereto. In this way, a disappearance rate of the enzyme in the body may be reduced, and stability of the enzyme may be enhanced to effectively treat a disease.

Hydrophilic, hydrophobic, water-soluble, and fat-soluble drugs may be used as the drug without any limitations. For example, the drug may be a low-molecular-weight synthetic compound, a low-molecular-weight natural compound, a peptide, a protein, an antibody, a therapeutic DNA, SiRNA, or a complex of the drug with another compound. The complex may include a mixture of a low-molecular-weight synthetic compound with an excipient, a physical complex or chemical complex (polymer-drug conjugate) of a low-molecular-weight synthetic compound with a polymeran electrostatic complex (polyion complex) of a peptide with a synthetic polymer, a protein impregnated into the exosome, an electrostatic complex (polyion complex) of a therapeutic DNA with a cationic polymer and the like, but the present invention is not limited thereto.

In addition, the present invention provides a method of preparing a hollow drug delivery system.

The method of preparing a hollow drug delivery system according to the present invention includes (a) cross-laminating a first polymer electrolyte and a second polymer electrolyte on surfaces of porous inorganic particles to prepare composite particles having a multilayer thin film coating layer formed thereon; and (b) dissolving the porous inorganic particles from the composite particles to form a hollow core.

The step (a) includes forming a coating layer on a surface of the core composed of the porous inorganic particles using the first polymer electrolyte and the second polymer electrolyte. In this case, the porous inorganic particles may be added into the first polymer electrolyte, and mixed with the first polymer electrolyte so that the first polymer can be attached to the surfaces of the porous inorganic particles. As one specific example, when the porous $CaCO_3$ particles are used in the core, $CaCO_3$ particles having a negative charge on surfaces thereof may be added to an aqueous gelatin solution, which is the first polymer electrolyte, and mixed using a known shaker so that the cationic gelatin can be attached to a surface of the core.

Next, after the gelatin-attached core is centrifuged and washed, the gelatin-attached core is added to an aqueous lignin or tannic acid solution, which is the second polymer electrolyte, and mixed with the aqueous solution to laminate the lignin or tannic acid. In particular, a coating layer of the multilayer thin film in which gelatin and lignin or tannic acid are cross-laminated may be formed by the complexation through electrostatic interaction between a hydroxyl group in the lignin and tannic acid and cationic group of the gelatin attached to the surface, and hydrophobic interaction between a phenolic group of the lignin and tannic acid and proline of the gelatin. In this case, the cross-laminating may be repeatedly performed once or more, particularly 2 to 10 times, but the method is not limited thereto.

Also, the step (a) may be performed by adjusting a pH value. For example, in the case of the drug delivery system according to the first aspect of the present invention, the gelatin has no charges at pH 7 to 9, and the lignin has a weak negative charge due to the hydroxyl group. Therefore, the coating layer may be formed in this pH range by the complexation through hydrophobic interaction between gelatin and lignin.

In addition, in the case of the drug delivery system according to the second aspect of the present invention, the gelatin in the coating layer has a positive charge at pH 4.5 to 5.5, and the tannic acid has a negative charge. Therefore, the coating layer may be formed in this pH range by the complexation through electrostatic interaction between gelatin and tannic acid.

The concentrations of the first polymer electrolyte and the second polymer electrolyte may be in a range of 0.1 to 10 mg/mL, particularly 0.5 to 5 mg/mL, and the prepared composite particles may include 1 to 10 parts by weight, particularly 2 to 5 parts by weight, each of the first polymer and the second polymer, based on 100 parts by weight of the porous inorganic particles, but this content range is not limited thereto.

The step (b) includes dissolving the porous inorganic particles using a chelating agent to prepare a hollow core having an empty inner space. As one specific example, the composite particles may be treated with an aqueous solution including the chelating agent to chelate calcium ($Ca^{2+}$) ions in the $CaCO_3$ particles, and thus to dissolve the porous $CaCO_3$ particles. In this case, the concentration of the aqueous chelate solution may be in a range of 0.01 to 10 M, particularly 0.1 to 5 M, and the pH value of the aqueous chelate solution may be in a range of pH 6.5 to 8, but the present invention is not limited thereto. After the porous inorganic particles are dissolved using the aqueous chelate solution, the porous inorganic particles may be centrifuged and washed to prepare the hollow drug delivery system particles including a hollow core and a coating layer of a multilayer thin film in which a first polymer and a second polymer are cross-laminated. The drug delivery system according to one aspect of the present invention include the hollow core having an empty inner space, and thus may remarkably improve an amount of the loaded drug in the core, and the loaded drug may stably move in the body by means of the coating layer so that a sufficient amount of the drug can reach a target region.

A method of preparing the hollow drug delivery system may further include containing the drug in pores of the porous inorganic particles. In particular, the containing of the drug in the pores of the porous inorganic particles may be carried out before the step (a). In this case, the drug may be loaded in the porous inorganic particles pores by the hydrophobic interaction by adding the porous inorganic particles into a solution in which the hydrophobic drug is dispersed and stirring the solution. Next, in the step (a) using the porous inorganic particles in which the drug is loaded, the coating layer is formed on surfaces of the porous inorganic particles to prepare composite particles. In the step (b), as the porous inorganic particles may be dissolved to prepare particles of the hollow drug delivery system in which the hydrophobic drug is loaded in the core, but the method is not limited thereto.

Also, when the drug is hydrophilic, the hollow core is formed through the steps (a) and (b). Then, the composite particle with hollow core may be added into an aqueous solution in which the hydrophilic drug is dispersed, and stirred so that the drug can be loaded in the hollow core and the coating layer. Also, the content of the drug in the solution and aqueous solution may be in a range of 0.01 to 5% by weight, particularly 0.01 to 3% by weight, but this content range is not limited thereto.

Further, the present invention provides a method of treating a disease, which includes administering a drug delivery system to deliver the drug delivery system to a lesion site, wherein the drug delivery system includes a core and a coating layer surrounding the core and composed of a multilayer thin film in which a first polymer electrolyte and a second polymer electrolyte are cross-laminated, characterized in that the first polymer electrolyte and the second polymer electrolyte are complexed by any one or more attractions selected from the group consisting of electrostatic interaction and hydrophobic interaction; and treating the drug delivery system with an enzyme.

In particular, after the drug delivery system in which the drug is loaded as described above is administrated together with the enzyme into the body through various routes of oral and parenteral administration, or the drug delivery system and the enzyme are separately administrated and delivered to a lesion site, the release of the drug may be induced using the degradation of the coating layer by the enzyme, which is expressed according to the pH change in the lesion site. More particularly, because the drug delivery system maintains a stable structure in sites having a pH value in a range of pH 6.5 to 9 in the body, the drug release may be suppressed to minimize the side effects of the drug. On the other hand, the coating layer may be degraded by the enzyme having a degradation activity in the lesion site having a pH value in a range of pH 4 to 6 to rapidly release the drug, thereby improving a therapeutic effect on a disease.

The disease may be any one selected from a cancer, an inflammatory disease, a skin disease, a metabolic disease. Preferably, the drug delivery system may be applied to cancer tissue cells having a relatively acidic pH range, and may be used to treat a cancer. Specific examples of the cancer may include skin cancer, melanoma, gastric cancer, esophageal cancer, colon cancer, colorectal cancer, pancreatic cancer, bowel cancer, rectal cancer, bile duct cancer, liver cancer, brain tumor, leukemia, sarcoma, bone cancer, breast cancer, thyroid cancer, lung cancer, uterine cancer, cervical cancer, endometrial cancer, prostate cancer, head and neck cancer, bladder cancer, endocrine cancer, urethral cancer, ovarian cancer, testicular cancer, renal cancer, lymphoma, and the like. As described above, when the drug delivery system is applied to treat cancer, the drug may be stably delivered without any early release of the drug in normal tissue cells having a pH value of pH 6.5 to 7. However, when the drug delivery system reaches cancer tissue cells having a relatively acidic condition of pH 5 to 6, the degradation activity of the enzyme may be expressed according to the pH change, and the coating layer may be degraded at the same time, thereby exhibiting rapid drug release characteristics. In this way, the drug delivery system may be used for the drug delivery system kit having an ability to target cancer so as to induce selective death of cancer cells, minimize side effects of anticancer drugs, and maximize a therapeutic effect on cancer as well.

Hereinafter, the present invention will be described in further detail with reference to Examples and Comparative Examples thereof. However, it should be understood that the following Examples and Comparative Examples are illustrative only to describe the present invention in detail, but are not intended to limit the scope of the present invention.

Preparation Example 1

Preparation of Porous Inorganic Particles

Porous inorganic particles were prepared using a co-precipitation method. Aqueous 0.33 M $CaCl_2$) (Sigma-Aldrich) and $Na_2CO_3$ (Sigma-Aldrich) solutions were mixed at a volume ratio of 1:1, and stirred at 600 rpm for 30 seconds. Thereafter, the resulting mixture was centrifuged at 10,000 rpm for 2 minutes, and then washed twice with distilled water to remove unreacted ions and residues, and thus to obtain porous $CaCO_3$ particles. Then, the porous $CaCO_3$ particles were freeze-dried for one day under reduced pressure to prevent recrystallization. The porous $CaCO_3$ particles thus obtained had an average particle diameter of 4 μm.

Preparation Example 2

Preparation of Drug Delivery System on Flat Substrate—1

A 20 mg/mL concentration of a gelatin (porcine skin-derived gelatin, Type A, Sigma-Aldrich) solution (pH 11) and fluorescein isothiocyanate isomer I (FITC, Sigma-Aldrich) were violently stirred overnight at 37° C. in 1 mL of dimethyl sulfoxide (DMSO), and then dialyzed against phosphate-buffered saline (PBS) for 5 days to prepare FITC-conjugated gelatin.

As shown in FIG. 1, a silicon wafer for quartz crystal microbalance (QCM) was treated with oxygen plasma for 2 minutes to form a negatively charged surface. Thereafter the silicon wafer was immersed in 100 mL of an 1 mg/mL concentration of aqueous FITC-conjugated gelatin solution (for 5 minutes to form a gelatin layer, and then washed twice with deionized water (DI water) for one minute. Then, a substrate on which the gelatin layer was laminated was immersed for 5 minutes in alkali lignin (weight average molecular weight: 20,000 g/mol, Sigma-Aldrich), which was dissolved at a concentration of 1 mg/mL in 1× phosphate-buffered saline (PBS, pH 7.4), to laminate a lignin layer (Preparation Example 2) formed by hydrophobic interaction with the gelatin layer, and then washed in the same manner. Subsequently, the gelatin and the lignin were cross-laminated three times to prepare a coating layer composed of multilayer thin film.

Preparation Example 3

Preparation of Drug Delivery System on Flat Substrate—2

A coating layer composed of a multilayer thin film, which was formed by cross-laminating gelatin and tannic acid on a silicon wafer substrate three times through the electrostatic interaction, was prepared in the same manner as in Preparation Example 2, except that the alkali lignin was replaced with tannic acid (TA, weight average molecular weight: 1,701 g/mol, Sigma-Aldrich) which was dissolved at a concentration of 1 mg/mL in deionized water (pH 5).

Preparation Example 4

Preparation of Hollow Drug Delivery System—1

40 mg of the porous $CaCO_3$ particles of Preparation Example 1 were put into 100 mL of an aqueous FITC-conjugated gelatin solution of 1 mg/mL concentration, and gelatin was attached to surfaces of the particles at 2,000 rpm for 5 minutes using a microtube shaker. Thereafter, the particles on which the gelatin layer was formed were centrifuged at 10,000 rpm for 2 minutes, a supernatant was removed, and was washed twice with deionized water for one minute. The particles were immersed for 5 minutes in alkali lignin (weight average molecular weight: 175,000 g/mol, Sigma-Aldrich) which was dissolved at a concentration of 1 mg/mL in 1× phosphate-buffered saline (PBS, pH 7.4) to form a lignin layer by means of the hydrophobic interaction with the gelatin layer, and then washed in the same manner. Cross-laminating of the gelatin and the lignin layer were repeatedly performed three times to form a coating layer composed of a multilayer thin film in which gelatin and lignin were cross-laminated three times, and thus to prepare a drug delivery system including a core composed of the porous $CaCO_3$ particles and a coating layer surrounding the core.

Figure 2:
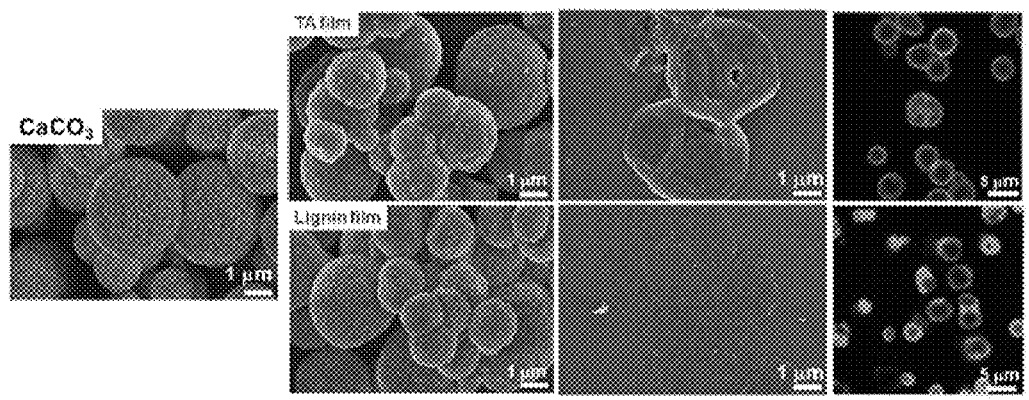
FIG. 2 shows fluorescence and scanning electron microscope (SEM) images of the drug delivery system according to one embodiment of the present invention.

Next, the drug delivery system was treated with a 0.2 M ethylenediaminetetraacetic acid (EDTA, Sigma-Aldrich) solution (pH 7.4) for approximately 3 minutes to chelate calcium in the core, and the porous $CaCO_3$ particles were then removed to obtain a hollow drug delivery system having an empty inner space. The resulting hollow drug delivery system was centrifuged at 10,000 rpm for 2 minutes, and then washed twice with distilled water to remove EDTA. The hollow drug delivery system was confirmed through SEM and fluorescence assays. As a result, as shown in FIG. 2, it can be seen that the $CaCO_3$ core particles had a porous structure, and were in a spherical shape having a size of approximately 3 to 5 μm. Also, it can be seen that the coating layer formed by cross-laminating gelatin and lignin on a surface of the core was prepared in the form of a thick film, and thus disappeared as the coating layer was covered with a surface of the core. In particular, it can be seen that, when the lignin was used, a coating layer having a smooth surface was formed. Even after the core was removed, and the hollow drug delivery system was prepared, the coating layer had a stable structure without any breakup of the coating layer.

Figure 3:
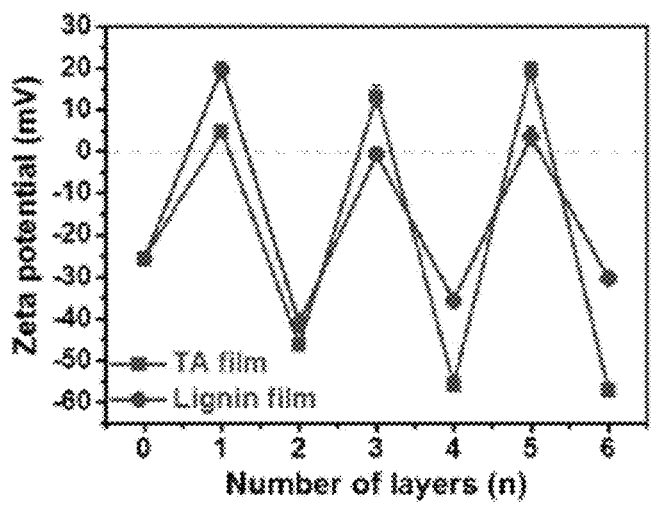
FIG. 3 is a graph of measuring a surface potential of the drug delivery system according to one embodiment of the present invention.

Also, as shown in FIG. 3, the zeta-potential was measured using SZ-100 (Horiba, Japan). As a result, it was confirmed that the surface potential of the core had a negative value, and gelatin having a positive charge may be easily absorbed thereinto. Also, it can be seen that the coating layer was stably laminated by repeatedly changing the surface potential as the coating layer is cross-laminated. In particular, it can be seen that the gelatin did not have high a positive charge, and thus did not have a high positive potential value, but the lignin was rich in hydroxyl groups in the molecular structure, and thus the surface potentials of the two layers of gelatin and lignin had a negative potential value, indicating very stable dispersibility (−30 to −40 mV).

Also, to confirm the degradation of the coating layer according to the pH and the enzyme, degrees of degradation of the coating layers were confirmed from a degree of detection of the released FITC-conjugated gelatin. In this case, a *Trametes versicolor* (≥0.5 U/mg)-derived laccase (Sigma-Aldrich) was used as the enzyme. Also, the coating layers were treated in a McIlvaine buffer whose pH value was adjusted to pH 5 and 7 using $Na_2HPO_4$ and citric acid, and divided into a total of 4 groups, which were used for experiments. Each of the experimental groups was stored for 7 days in a 37° C. incubator, and the supernatants were extracted after a predetermined time. Then, the emission of fluorescence intensity was measured through photoluminescence (PL; PF-8300, Jasco, Easton, Md., USA), and the residual fluorescence intensity was evaluated using a confocal microscope (Leica, Germany).

Figure 4:
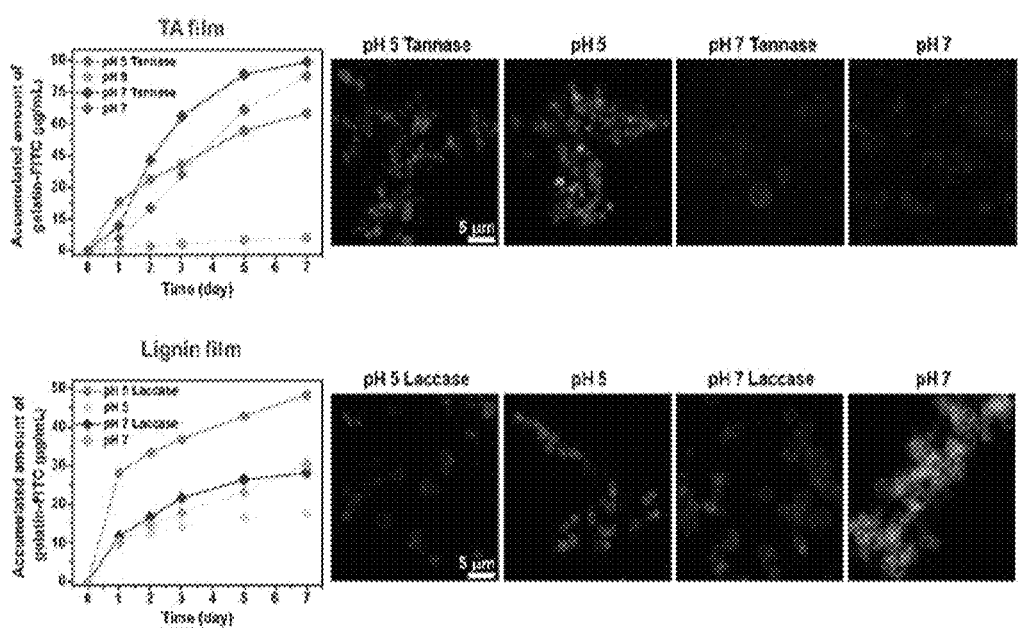
FIG. 4 shows a graph and a fluorescence image showing a degradation of the drug delivery system according to one embodiment of the present invention according to the pH and an enzyme.

As a result, as shown in FIG. 4, it can be seen that the coating layers treated with the laccase at pH 5 were most rapidly degraded, and it can also be seen that the coating layers were not severely degraded at pH 7 and when the coating layers were not treated with the laccase. These results were also confirmed from a fluorescence image. From the results, it can be seen that that fluorescence signals of the coating layers treated with the laccase at pH 5 were the weakest, and it can also be seen that, when the coating layers were not treated with the enzyme, the shapes and fluorescence intensities of the coating layers were stably maintained for 7 days. From these results, it was confirmed that the coating layers were easily degraded because the laccase had a higher enzymatic activity at pH 5, compared to pH 7.

Preparation Example 5

Preparation of Hollow Drug Delivery System—2

A tannic acid layer was formed by the electrostatic interaction with the gelatin layer in the same manner as in Preparation Example 4, except that the alkali lignin was replaced with tannic acid (TA, weight average molecular weight: 1,701 g/mol, Sigma-Aldrich) which was dissolved at a concentration of 1 mg/mL in deionized water (pH 5) during formation of the coating layer. Then, a hollow drug delivery system having an empty inner space was obtained by cross-laminating three times and forming chelate bonds.

The hollow drug delivery system was confirmed through the SEM and fluorescence assays. As a result, as shown in FIG. 2, it was confirmed that the coating layer formed by cross-laminating of gelatin and tannic acid had a very rough surface, compared to the coating layer of Preparation Example 4, and that the coating layer had a stable structure without any breakup of the coating layer even after the core was removed to prepare the hollow drug delivery system.

Also, as shown in FIG. 3, the zeta-potential was measured using SZ-100 (Horiba, Japan). As a result, it can be seen that the coating layer was stably laminated, and it was also confirmed that the tannic acid was rich in hydroxyl groups in the molecular structure, and thus the surface potentials of the two layers of gelatin and tannic acid had a negative potential value, indicating very stable dispersibility (40 to 60 mV).

Also, the degradation of the coating layer was confirmed according to the pH and the enzyme. As a result, as shown in FIG. 4, it can be seen that the coating layer was not degraded at all for 7 days when the coating layer was not treated with the tannase at pH 5, and the coating layer was rapidly degraded at pH 7 and when the coating layer was treated with the tannase. It can be seen that, when a degree of fluorescence remaining after 7 days was confirmed, the highest fluorescence intensity was observed at pH 5, and, in the other cases, the degrees of fluorescence were highly reduced due to the severe degradation of the coating layers. From these results, it was confirmed that the coating layer was easily degraded because the tannase had the highest enzymatic activity at pH 5, and the coating layer was not degraded by the enzyme because the tannase had a low enzymatic activity at pH 7. This indicated that tannic acid was spontaneously oxidized with an increasing pH value so that it has a quinoide structure, and hydroxyl radicals were formed. As a result, it was confirmed that the coating layer was degraded since the attraction of tannic acid to gelatin disappeared as the tannic acid was spontaneously degraded at pH 7.

Experimental Example 1

Drug Release Test 1 mL of doxorubicin hydrochloride (DOX-HCl, Sigma-Aldrich) was added at a concentration of 0.5 mg/mL, and stirred at 1,000 rpm for one day to load a drug in the pores of the porous $CaCO_3$ particles and the coating layers prepared in Preparation Examples 4 and 5. Thereafter, a hollow drug delivery system was prepared through a chelate bond to check an amount of released drug. In particular, 5 mg of the hollow drug delivery system was dispersed in buffers (pH 5 and 7) including 1 mg/mL of laccase (Preparation Example 4) or tannase (Preparation Example 5) and buffers (pH 5 and 7) including no enzyme. The prepared drug delivery systems were centrifuged at 10,000 rpm for 2 minutes to remove supernatants from which DOX was released, and an equivalent amount of a fresh buffer was added thereto. An amount of the released DOX was measured using PF-8300 (Jasco, Easton, Md., USA), and the accumulated amount of released drug was calculated.

Figures 5, 6:
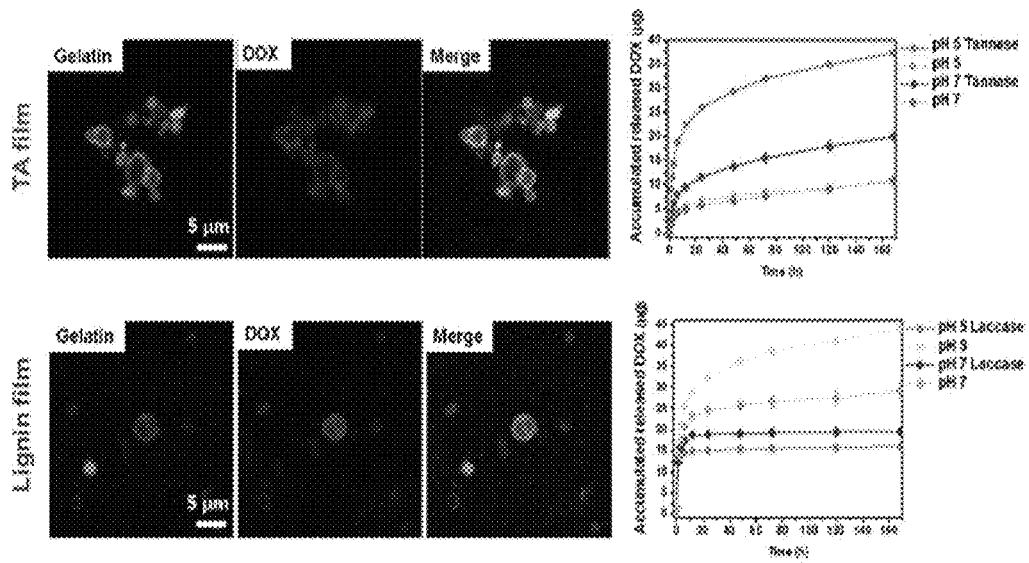
FIG. 5 shows a fluorescence image and a graph of measuring an amount of the drug released after the drug is loaded in the drug delivery system according to one embodiment of the present invention.
FIG. 6 shows the test results of cytotoxicity of the drug delivery system according to one embodiment of the present invention.

The drug delivery systems were assayed using a confocal microscope. As a result, as shown in FIG. 5, it can be seen that the entire DOX (red fluorescence) was loaded in the coating layer and the core of the drug delivery system (green fluorescence). Loading the DOX in the coating layer indicates that some hydrophobic moieties of the DOX and some hydrophobic moieties of the tannic acid or lignin in the coating layer were combined with each other by the hydrophobic interaction.

Next, the degrees of DOX release were confirmed according to the pH and the treatment with an enzyme. As a result, the results shown in the graph of FIG. 5 assumed that, when Preparation Example 4 was treated with the laccase, the DOX served as a mediator to enhance polymerization efficiency of the laccase, thereby inhibiting the drug release at pH 5.

Also, it was confirmed that, when Preparation Example 5 was treated with the tannase, the most rapid drug release efficiency was observed at pH 5 unlike Preparation Example 4 treated with the laccase, and the DOX hindered the self-oxidation of tannic acid at pH 7 to reduce the drug release.

Experimental Example 2

Cytotoxicity Test and Confirmation of Anticancer Effect

HeLa cells were cultured for 2 to 3 days in a 100 mm culture dish (SPL, Pocheon-si, Korea) in a 5% $CO_2$ incubator. When 95% of the cells were grown, the cells were detached by trypsin-EDTA treatment. Thereafter, for a toxicity test, the cells were inoculated at a density of 7,000 cells/well in a 24-well plate. For cell attachment, the cells were cultured for one day, and for cytotoxicity and anticancer assays, the enzyme, DOX, and DOX-free hollow drug delivery system in the culture medium were used to treat the cells separately. After the materials were cultured for one day, the cytotoxicity was measured using a 3-(4,5-dimethylthiazol-2-yl)-2,5-diphenyltetrazolium bromide (MTT) assay. An MTT solution (5 mg/mL) in PBS was used to treat the cells for 2 hours in an incubator, the cells were dissolved in DMSO, and the absorbance at a wavelength of 540 nm was measured using a plate reader (SpectraMax 340 PC; Molecular Devices, Sunnyvale, Calif., USA).

The anticancer effect of the DOX-conjugated drug delivery system was investigated through a cytotoxicity test. In this case, 1 µg of the DOX-conjugated hollow drug delivery systems of Preparation Examples 4 and 5 were used. A cell culture medium was composed of 90% Dulbecco's Modified Eagle Medium, 10% fetal bovine serum, and 1% penicillin-streptomycin-glutamine. All the products were purchased from GibcoLife Technologies (Grand Island, N.Y., USA), and acetic acid was used to adjust the pH value of Dulbecco's Modified Eagle Medium to pH 5.5.

The cytotoxicity tests were performed for the hollow drug delivery systems of Preparation Examples 4 and 5. As a result, as shown in FIG. 6, it was confirmed that the hollow drug delivery systems had no toxicity because the cells had a cell viability of 90% or more.

Figure 7:
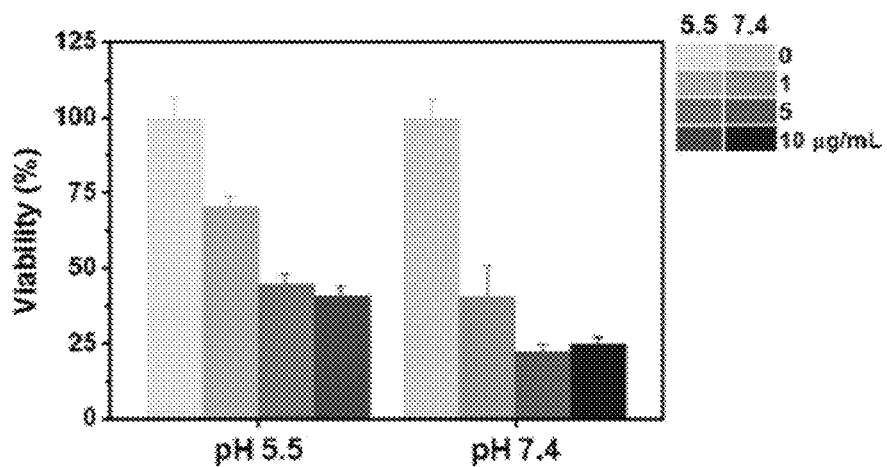
FIG. 7 shows the test results of cytotoxicity of the drug delivery system according to one embodiment of the present invention according to the concentration of a drug and the pH.
Figure 8:
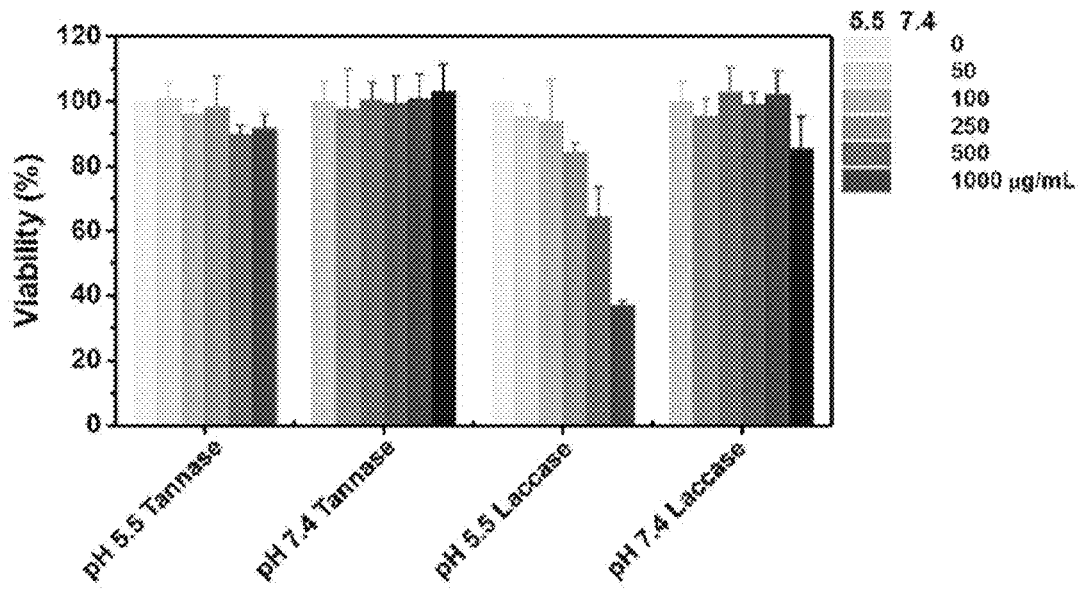
FIG. 8 shows the test results of cytotoxicity of a drug delivery system kit according to one embodiment of the present invention according to the concentration of an enzyme and the pH.

Also, FIGS. 7 and 8 are graphs illustrating the cytotoxicities of DOX and an enzyme used, respectively. It was confirmed that the DOX had very high toxicity even when used at an amount of 1 µg. Also, it was confirmed that, when the cytotoxicities of the enzymes were checked, the enzymes other than the laccase had no toxicity when used at a very high enzyme concentration of 1 mg/mL at pH 5.5.

Therefore, in the present invention, the amounts of the enzymes treated for the drug release were set to 100 µg and 250 µg in the case of the laccase and the tannase, respectively. Each of the enzymes was applied to Preparation Examples 4 and 5 to check the anticancer effects.

As a result, as shown in FIG. 9, it was confirmed that the laccase-treated drug delivery system had an excellent anticancer effect in the case of Preparation Example 4, and that the tannase-treated drug delivery system had an excellent anticancer effect at pH 7.4 in the case of Preparation Example 5, indicating that the anticancer effects may be controlled in a desired fashion according to the degree of drug release.

The drug delivery system kit according to the present invention has advantages in that the drug delivery system kit has no toxicity, exhibits high stability in the body, and may deliver the drug to a lesion site, thereby preventing the early leakage of the drug and minimizing the side effects on tissues other than the lesion site.

Also, the drug delivery system kit according to the present invention has advantages in that the drug delivery system kit has a large amount of the loaded drug, and simultaneously further maximize the therapeutic effect because it is possible to realize the selective release of the drug using the enzyme having a degradation activity against the drug delivery system.

In particular, the drug delivery system kit according to the present invention has advantages in that the drug delivery system kit may be applied to cancer cells with weak acidity to effectively kill the cancer cells because it is possible to effectively release the drug from the drug delivery system using the enzyme having a degradation activity in a weak acidic range.

What is claimed is:

1. A drug delivery system kit comprising:
   a drug delivery system comprising a core and a coating layer surrounding the core and composed of a multi-layer thin film in which a first polymer electrolyte thin film and a second polymer electrolyte thin film are cross-laminated; and
   an enzyme,
   wherein the core of the drug delivery system comprises porous inorganic particles;
   wherein the first polymer electrolyte thin film is formed on a surface of the inorganic particles;
   wherein the first polymer electrolyte comprises an ionic polypeptide, and the second polymer electrolyte comprises an enzymatically degradable phenolic polymer; and
   wherein the first polymer electrolyte and the second polymer electrolyte are complexed by any one or more attractions selected from the group consisting of electrostatic interaction and hydrophobic interaction.

2. The drug delivery system kit of claim 1, wherein the enzyme has a degradation activity against the coating layer of the drug delivery system.

3. The drug delivery system kit of claim 1, wherein the core of the drug delivery system comprises a hollow core having an empty inner space.

4. The drug delivery system kit of claim 1, wherein the second polymer electrolyte comprises lignin.

5. The drug delivery system kit of claim 1, wherein, when the drug delivery system comes into contact with the enzyme, release of a drug is suppressed in a range of pH 6.5 to 9, and the drug is rapidly released in a range of pH 4 to 6.

* * * * *